United States Patent
Ross et al.

(10) Patent No.: US 6,175,004 B1
(45) Date of Patent: Jan. 16, 2001

(54) PROCESS FOR THE SYNTHESIS OF OLIGONUCLEOTIDES INCORPORATING 2-AMINOADENOSINE

(75) Inventors: Bruce S. Ross; Muthiah Manoharan, both of Carlsbad, CA (US)

(73) Assignee: Isis Pharmaceuticals, Inc., Carlsbad, CA (US)

( * ) Notice: Under 35 U.S.C. 154(b), the term of this patent shall be extended for 0 days.

(21) Appl. No.: 09/144,883

(22) Filed: Sep. 1, 1998

(51) Int. Cl.$^7$ .................................................. C07H 21/00
(52) U.S. Cl. ................. 536/25.3; 536/25.31; 536/25.32; 536/25.33; 536/25.34
(58) Field of Search ............................... 536/25.3, 25.31, 536/25.32, 25.33, 25.34

(56) References Cited

U.S. PATENT DOCUMENTS

| | | | |
|---|---|---|---|
| 4,835,263 | * 5/1989 | Nguyen et al. | 536/24.3 |
| 5,034,506 | 7/1991 | Summerton et al. | 528/391 |
| 5,138,045 | 8/1992 | Cook et al. | 536/27 |
| 5,142,047 | * 8/1992 | Summerton et al. | 544/118 |
| 5,210,264 | 5/1993 | Yau | 558/167 |
| 5,218,105 | 6/1993 | Cook et al. | 536/25.31 |
| 5,459,255 | 10/1995 | Cook et al. | 536/27.13 |
| 5,470,974 | * 11/1995 | Summerton et al. | 544/118 |
| 5,474,929 | * 12/1995 | Pelcher | 435/172.3 |
| 5,506,351 | * 4/1996 | McGee | 536/55.3 |
| 5,514,786 | * 5/1996 | Cook et al. | 536/23.1 |
| 5,539,082 | 7/1996 | Nielsen et al. | 530/300 |
| 5,672,695 | * 9/1997 | Eckstein et al. | 536/24.5 |
| 5,696,255 | 12/1997 | Vorbrüggen et al. | 536/55.3 |
| 5,698,687 | * 12/1997 | Eckstein et al. | 536/25.3 |
| 5,795,714 | * 8/1998 | Cantor et al. | 435/6 |
| 5,817,635 | * 10/1998 | Eckstein et al. | 514/44 |

FOREIGN PATENT DOCUMENTS

WO 92/20823  11/1992 (WO).

OTHER PUBLICATIONS

Abid, et al., "A High–Yield Synthesis of Deoxy–2–Fluroinosine and its Incorporation into Oligonucleotides", *Tetra. Lett.,* 1997, 38(17), 2989–2992.

Alul, R.H. et al., "Oxalyl–CPG: a labile support for synthesis of sensitive oligonucleotide derivatives", *Nucl. Acid Res.,* 1991,19,1527–1532.

Bailly, C. et al., "PCR–based development of DNA substrates containing modified bases: An efficient system for investigating the role of the exocyclic groups in chemical and structural recognition by minor groove binding drugs and proteins", *Proc. Natl. Acad. Sci. USA.,* 1996, 93, 13623–13628.

Barabino, S.M. et al., "Antisense probes targeted to an internal domain in U2 snRNP specifically inhibit the second step of pre–mRNA splicing", *Nucl. Acids Res.,* 1992, 20(17), 4457–4464.

Brown et al., "The Incorporation of 2,6–Diaminopurine into Oligodeoxyribonucleotides by the Phosphoramidite Method", *Nucleosides Nucleotides,* 1989, 8(5&6) 1051.

Cano et al., "Synthesis of Oligodeoxyribonucleotides Containing 2,6–Diaminopurine", *Nucleosides Nucleotides,* 1994,13(1–3), 501–509.

Chollet et al., "Synthesis of Oligdeoxyribonuecleotides Containing the Base 2–Aminoadenine", *Chemica Scripta,* 1986, 37–40.

Crooke, S.T. et al., "Pharmacokinetic Properties of Several Novel Oligonucleotide Analogs in mice",*J.Pharmocol. Exp. Therapeutics,* 1996, 277, 923–937.

Gaffney, B.L. et al., "The Influence of the Purine 2–Amino Group on DNA Conformation and Stability–II", *Tetrahedron,* 1984, 40 3–13.

Gebeyehu, G. et al., "Novel bitinylated nucleotide –analogs for labeling and colorimetric detection of DNA", *Nucl. Acids Res.,* 1987,15, 4513–4534.

Gryaznov, S. et al., "Stabilization of DNA:RNA Duplexes by Substitution of 2'–deoxyadenosine with 2'–deoxy2–aminoadenosine", *Tetrahedron Letts.,* 1994, 35, 2489–2492.

kabanov, A. V., "A new class of antivirals: antisense olgonucleotides combined with a hydrophobic substituent effectively inhibit influenza virus reproduction and synthesis of virus–specific proteins in MDCK cells "*FEBS Letts.,* 1990, 259 327–330.

Kornberg, A., *DNA Replication,* W.H. Freeman and Co., San Francisco, 1980, 75–77.

Krolikiewicz et al., "The Synthesis of 2–Fluoropurine Nucleosides", *Nucleosides & Nucleotides,* 1994, 13(1–3), 673–678.

Lamm et al., "Antisense probes containing 2–aminoadenosine allow efficient depletion of U5 snRNP from HeLa splicing extracts", *Nucl. Acids Res.,* 1991,19(12), 3193–3198.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.,* 1989, 86, 6553–6556.

(List continued on next page.)

*Primary Examiner*—James O. Wilson
(74) *Attorney, Agent, or Firm*—Woodcock, Washburn Kurtz Mackiewicz & Norris LLP

(57) ABSTRACT

This invention presents novel processes for incorporating 2-aminoadenosine and 2-aminoadenosine analogs into oligonucleotides. A halogenated adeninosine is incorporated into an oligonucleotide using standard synthesis methods, such as phosphoramidited protocols. Subsequent reaction with an amine results in the desired product. The oligonucleotides produced provide stronger hybridization to their target sequences. These oligonucleotides can be useful compounds, inter alia for diagnostic and therapeutic applications.

15 Claims, No Drawings

OTHER PUBLICATIONS

Luyten et al., "Protection of 2,'–Diaminopurine 2'–Deoxyriboside", *Nucleosides Nucleotides,*1997,16(7–9), 1649–1652.

Manoharan M. et al., "Cholic Acid–Oligonucliotide Conjugates for Antisense Applications", *Bioorganic Med. Chem. Letts.,*1994, 4, 1053–1060.

Manoharan, M. et al., "Chemical Modifications to Improve Uptake and Bioavailability of Antisense Olignucleotides", *Annals NY Acad. Sciences,* 1992, 660, 306–309.

Manoharan M. et al., "Oligonucleotide Conjugates: Alteration of the Pharmacokinetic Properties of Antisense Agents", *Nucleosides and Nucleotides,* 1995, 14, 969–973.

Manoharan, M. et al.,"Oligonucleotides Bearing Cationic Groups: N2–(3–Aminopropyl) deoxyguanosine Synthesis, Enhanced Binding Properties and Conjugation Chemistry ", *Tetrahedron Letters,* 1996 37, 7675–7678.

Manoharan, M. et al., "Introduction of a Lipophilic Thioether Tether in the Minor Groove of Nucleic Acids for Antisense Applications", *Bioorg. Med. Chem. Letts.,* 1993, 3, 2765–2770.

Manoharan, M. et al., "Lipidic Nucleic Acids ", *Tetrahedron Letts.,* 1995, 36, 3651–3654.

Martin, P., "Ein neuer Zugang zu 2'–O–Alkyyribonucleosiden und Eigenschaften deren Olignucleotide", *Helvetica Chemica Acta,* 1995, 78, 486–504.

Mishra, R.K. et al., "Improved leishmanicdal effect of phosphorotioate antisense oligonuvleotides by LDL–mediated delivery ", *Biochim. Et Biophysica ,*1995. 1264, 229–237.

Nielsen, P.E. et al., "Sequence–Selective Recognition of DNA by Strand Displacement with a Thymine–Substituted Polyamide", *Science,* 1991, 254 1497–1500.

Oberhauser, B. et al., "Effective incoporation of 2'–O–methyl–oliognucleotides into liposomes and enhanced cell association through modification with Thiocholesterol", *Nucl. Acids Res.,* 1992. 20, 533–538.

Saison–Behmoaras, T. et al., "Short modified antisense oligonucleotides directed against Ha–ras point mutation induce selective cleavage of the mRNA and inhibit T24 cells proliferation", *EMBO J.,* 1991,10,1111–1118.

Shea, R.G. et al., "Synthesis, hybridization properties and antiviral of activity lipidoligodeoxynucletide conjugates", *Nucl. Acids Res.,* 1990,18, 3777–3783.

Svinarchuk, F.P. et al., "Inhibition of HIV proliferation in MT–4cells by antisense olignoucleotide conjugated to lipophilic groups ", *Biochimie,* 1993 79, 49–54.

Wright, P. et al., "Large Scale Synthesis of olionucleotides via phosphoramidite Nucleosides and a High–loaded Polystyrene Support", *Tetrahedron Letts.,* 1993, 34, 3373–3376.

Agrawal, S. (ed.), *Protocols for Oligonucleotides and Analogs,* Humana Press, Totowa, N J, 1993.

Ausubel, F.M. et al., (eds.), *Current Protocols in Molecular Biology,* Current Publications, 1993.

Green and Wurs, *Protective Groups in Organic Synthesis ,* 2 ed., John Wiley & Sons, New York, 1991.

Manoharan, M., *Antisense Research and Applications,* Crooke et al., (eds.), CRC Press, Boca Raton, 1993.

Sambrook, J. et al., (eds), *Molecular Cloning , A laboratory Manual,* Second Ed., Cold Spring Harbor Laboratory Press, 1989.

* cited by examiner

PROCESS FOR THE SYNTHESIS OF OLIGONUCLEOTIDES INCORPORATING 2-AMINOADENOSINE

FIELD OF THE INVENTION

This invention is related to synthesis of oligonucleotides. In accordance with preferred embodiments this invention provides improved processes for the synthesis of oligonucleotides incorporating 2-aminoadenosine and similar moieties.

BACKGROUND OF THE INVENTION

Oligonucleotides and their analogs have been developed for various uses in molecular biology, including use as probes, primers, linkers, adapters, and gene fragments. In a number of these applications, the oligonucleotides specifically hybridize to a target nucleic acid sequence. Hybridization is the sequence specific hydrogen bonding of oligonucleotides via Watson-Crick and/or Hoogsteen base pairs to RNA or DNA. The bases of such base pairs are said to be complementary to one another.

One method of use for oligonucleotides is the inhibition of specific gene expression, where the oligonucleotides are complementary to specific target messenger RNA (mRNA) or other sequences. This mode of action is commonly known as "antisense". The specific binding of an antisense oligonucleotide to its target mRNA or other sequence can inhibit gene expression by at least two major mechanisms. The binding of the oligonucleotide to its target may hinder protein binding for translation and/or regulation. Moreover, the oligonucleotides may act through RNase-mediated degradation of a DNA/RNA duplex. Antisense technology is used in research applications to study the functions of certain genes. Antisense oligonucleotides can also be therapeutic agents, with one antisense drug having been approved for use and several oligonucleotides currently undergoing clinical trials.

Phosphorothioate oligonucleotides, which incorporate a phosphorothioate linkage (P=S), as opposed to a phosphodiester linkage (P=O), are presently being used as antisense agents in human clinical trials for various disease states, including use as antiviral, anticancer and anti-autoimmune agents.

Oligonucleotides have also found use in the diagnostic testing of materials including, for example, biological fluids, tissues, intact cells and isolated cellular components. As with gene expression inhibition, diagnostic applications can utilize the ability of oligonucleotides to hybridize with a complementary strand of nucleic acid. There are numerous examples of commercially available kits using probe technologies that hybridize to a target sequence for diagnostic purposes.

Oligonucleotides are also widely used as research reagents. They are particularly useful in studies exploring the function of biological molecules, as well as in the preparation of biological molecules. For example, the use of both natural and synthetic oligonucleotides as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR.

Oligonucleotides are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Representative uses include synthetic oligonucleotide probes, screening expression libraries with antibodies and oligonucleotides, DNA sequencing, In Vitro Amplification of DNA by the Polymerase Chain Reaction and Site-directed Mutagenesis of Cloned DNA. See Book 2 of *Molecular Cloning, A Laboratory Manual*, supra, and DNA-Protein Interactions and The Polymerase Chain Reaction, Vol. 2 of *Current Protocols In Molecular Biology*, supra.

It is greatly desired that oligonucleotides be able to be synthesized to have customized properties which are tailored for desired uses. Thus a number of chemical modifications have been introduced into oligonucleotides to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Oligonucleotides bind in a sequence specific manner to their target, a stretch of nucleotides from either DNA or RNA, especially messenger RNA (mRNA). The base-pairing of such interactions is the well known; A-T (or A-U) and G-(C base pairing. The G-C base pair provides three hydrogen bonds, while the A-T and A-U base pairs provide only two. Thus, the A-T base pair is energetically less favorable. By increasing the A-T base pair to have three hyrogen bonds, through chemical modification of these bases, it has been shown that a more stable duplex structure can be formed.

This increased hybridization is expected to have wide-reaching application in molecular biology. Diagnostic probes and therapeutic agents are expected to be more effective.

The incorporation of 2-aminoadenosine (2,6-diaminopurine) and similar moieties into oligonucleotides in place of adenosine provides an additional site for hydrogenbonding to uridine or thymidine. This modification has been shown to increase the binding affinity of oligonucleotides to their target RNA sequences and, to a lesser extent, DNA sequences (Gryaznov, S., et al., *Tetrahedron Lett.* 1994, 35, 2489–2492).

The use of oligonucleotides containing 2-aminoadenosine has been described in Lamm, G. M., et al. (*Nucleic Acids Res.* 1991, 19, 3193–3198) and Barabino, S. M., et al., (*Nucleic Acids Res.* 1992, 20, 4457–4464) wherein 2'-O-allyl antisense probes containing 2-aminoadenine were used to deplete U5 snRNP from cell extracts and to inhibit exon ligation. Oligonucleotides without 2-aminoadenosine were less effective.

Despite the benefit of enhanced hybridization, from such modification, oligonucleotides incorporating such substitutions have not been widely used due to the difficulty of incorporating 2-modified aminoadenosines into oligonucleotide chains. It has been particularly difficult to devise a protection scheme which is stable to chemical and oligonucleotide synthesis, yet can be cleanly removed during a normal deprotection cycle on a DNA synthesizer. The two exocyclic amines on the moieties have very different electronic properties and therefore different protection/deprotection properties; the N2 is electron rich and the N6 is electron poor. From an empirical point of view, when they are both protected as amides (e.g. isobutyryl), the N6 comes off very easily such that dilute basic solutions will cause partial deprotection and lower the isolated yield of the bis protected nucleotide. Once the N6 is deprotected, the N2 is extremely stable and is therefore difficult to remove.

A wide variety of methods have been used to produce oligonucleotides containing 2-aminoadenosine. Gaffney, B. L., et al. (*Tetrahedron* 1984, 40, 3–13) prepared short hexamer and octomer sequences incorporating 2-aminoadenine by protecting with N-acyl. However, this synthesis method did not allow the incorporation of multiple 2-aminoadenine residues into an oligonucleotide of defined sequence.

Chollet, A., et al. (*Chemica Scripta* 1986, 26, 37–40) prepared 2-aminoadenosine phosphoroamidites and phosphotriesters by protecting the N2 position of adenine with isobutyryl and the N6 position with 1-methyl-2,2-diethoxy pyrrolidine. The monomers were incorporated in an oligonucleotide chain using standard synthesis methods. However, deprotection of the N2 amide required prolonged incubation with $NH_4OH$, up to a week.

Other protecting groups used have included n-butylformamide (Brown, T., et al., *Nucleosides and Nucleotides* 1989, 8, 1051), bisphenoxyacetyl (Gryaznov. S., et al., *Tetrahedron Lett.* 1994, 35, 2489–2492), phenoxy-acetal (Cano, A., et al., *Nucleosides and Nucleotides* 1994, 13, 501–509) and dimethylformamide (Luyten, I., et al., *Nucleosides and Nucleotides* 1997, 16, 1649–1652). However, with all of these protecting groups, either lengthy deprotecting times were needed or low yields were seen.

PCR has also been used to incorporate 2-aminoadenosine into DNA (Bailly, C., et al., *Proc. Natl. Acad. Sci. USA* 1996, 93, 13623–13628). Although yields are expected to be good, this process is not amenable to oligonucleotide sequences of the length commonly used in antisense and other diagnostic and therapeutic applications nor to the scales necessary for use as drugs.

Thus, there remains a need for improved methods for incorporating 2-aminoadenosine into oligonucleotides, especially those with sequence specificity.

SUMMARY OF THE INVENTION

In accordance with this invention there are provided processes for the synthesis of oligonucleotides comprising 2,6-disubstituted purine heterocycles of the formula (I):

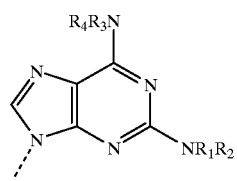

(I)

Where $R_1$, $R_2$, are, independently, H, unsubstituted or substituted hydrocarbyl group having from 1 to about 30 carbon atoms. $R_1$ and RR may also be a 5 to 13 membered ring or ring system, optionally incorporating additional heteroatoms selected from N, O and S.

$R_3$ and $R_4$ are also, independently, H, unsubstituted or substituted hydrocarbyl group having from 1 to about 30 carbon atoms. $R_1$ and $R_4$ may also be a 5 to 13 membered ring or ring system, optionally incorporating additional heteroatoms selected from N, O and S.

The methods of the invention comprise reacting an oligonucleotide comprising a 2-halo 6-substituted purine heterocycle having general formula [III]

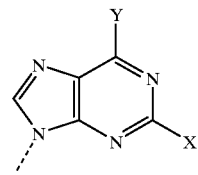

(II)

wherein X is halogen; Y is halogen, $NR_3R_4$ or $NR_3Pg$; $R_3$ and $R_4$ are as previously defined; and Pg is an amino protecting group. The moiety is reacted with an amine capable of converting the 2-halo 6-substituted purine heterocycle of formula [II] to a heterocycle of formula [I].

DESCRIPTION OF PREFERRED EMBODIMENTS

The processes of the present invention are useful for the synthesis of oligonucleotides incorporating 2-aminoadenosine and 2-aminoadenosine and like moieties into oligonucleotides. The resulting oligonucleotides provide stronger hybridization to their target sequences and are important compounds for diagnostic, therapeutic and other applications.

The processes of the present invention provide efficient production of oligonucleotides incorporating 2-aminoadenosine and related moieties. The processes are amenable to both small and large scale synthesis of oligonucleotides incorporating 2-aminoadenosines.

For the purposes of the present invention, 2-aminoadenosine and 2-aminoadenosine analog moieties include 2-aminoadenosine as well as N2 substituted 2-aminoadenosine analogs such as those described in U.S. Pat. No. 5,459,255, commonly assigned and herein incorporated by reference. Also included are N6 substituted 2-aminoadenosine analogs. A number of substituent groups can be introduced into 2-aminoadenosine in a protected (blocked) form or otherwise subsequently incorporated into an oligonucleotide and de-protected if necessary to form a final, desired compound. Substituent groups include groups covalently attached to the purine ring.

It will be appreciated that 2-aminoadenosine, comprise the 2-modified heterocyclic base (Adenine) attached in the convenient way to a sugar moiety. Such 2-amino modified adenosines can be incorporated into oligonucleotides in ways well known to persons of ordinary skill in the art, especially via automated methods. While the chemical modifications disclosed herein operate upon the heterocyclic nitrogen compound, the more complex adenosine is the usual chemical specie desired for incorporation and use. Other structures such as those employing modified sugars, modified nucleotide bond and otherwise are also useful herein.

Substituients at the amino functions of the adenosine are represented as $R_1, R_2$, $R_3$ and $R_4$ which include hydrocarbyl groups such as alkyl or substituted alkyl, alkenyl or substituted alkenyl, alkynyl or substituted alkynyl, cycloalkyl, cycloalkenyl, cycloaralkyl, aryl, aralkyl or substituted aralkyl. Preferably, $R_1$ to $R_4$ are independently alkyl, alkenyl and alkynyl substituent, collectively hydrocarbyls, groups having from 1 to about 30 carbons, with 1 to about 10 carbons being particularly preferred. Preferably, the aryl groups have from 6 to about 14 carbons, and aralkyl groups have from 7 to about 30 carbons. The substituent groups listed above can themselves bear substituent groups such as alkoxy, hydroxyl, amine, benzyl, phenyl, nitro, thiol, thioalkoxy, halogen, or alkyl, aryl, alkenyl, or alkynyl groups, and ether groups. Examples of alkyl substitutions are further disclosed by Manoharan, 14., *Antisense Research and Applications*, Crooke and Lebleu, eds., CRC Press, Boca Raton, 1993. Amine substituents include $NH_2$, polyalkylamines, aminoalkylamines, hydrazine, i.e. (—NH—NH—), hydroxylamines i.e. (—NH—OH), semicarbazides i.e (—NH—C(O)—NH—$NH_2$), thiosemicarbazides i.e (—NH—C(S)—NH—$NH_2$), hydrazones i.e. (—N=NH), or hydrazides i.e. (—C(O)—$NHNH_2$), imidazoles, imidazole amides, alkylimidazoles, tetrazole, and triazole.

In a particulary preferred embodiment, R; is H and $R_2$ is a group selected from a substituted aminoalkyl, (especially —$(CH_2)_n$—$N[CH_2)$,$NH_2]_{1-2}$, wherein n=0 to 30, e.g. dimethylaminoethyl, —$(CH_2)_2$—$N[CH_2)_2NH_2]_{1-2}$ wherein n=0 to 30, phthalimidoalkyl (e.g. phthalimidoethyl), imidazolylalkyl (e.g. imidazolylethyl) and piperazinylalkyl (e.g. piperazinylethyl).

$R_1$ and $R_2$, or $R_3$ and $R_4$ may optionally form a 5 to 13 membered ring or ring system optionally incorporating additional heteroatoms selected from N, O and S. Such rings or ring systems may include additional purine heterocycles. Preferred are rings without additional heteroatoms and rings with a single N. Preferred are rings containing 5 to 7 members. Most preferred are rings with 6 members. The rings may also contain unsaturated bonds.

X of formula (II) may be any halogen, preferred F or Cl. Most preferred is F. Y of general formula [II] may be a halogen or may be a compound of formula $NR_3R_4$. Additionally, protecting groups may be added to $NR_3R_4$. However, protecting groups on $NR_3R_4$ may not be necessary for substitutions such as secondary or tertiary amines. The electron withdrawing effect of the halogen group may make the N6 even more electron poor. When deprotecting with ammonium hydroxide, the halogen at the N2 position is converted to an amine while the substituents $R_3$ and $R_4$ at the N6 position are unchanged. The steps required to add protecting groups at the N6 position are generally not performed. When protecting groups at the N6 position are present, they may unintentionally come off during the workup after the N protection step, DMT and phosphoramidite reactions. Since, after each step it is necessary to purify the desired product, additional steps would be introduced in the process and overall yields are reduced. Therefore, unprotected forms of $NR_3R_4$ are preferred. Most preferred is the unprotected $NH_2$ at the N6 position.

In general, protecting groups render chemical functionality inert to specific reaction conditions and can be appended to and removed from such functionality in a molecule without substantially damaging the remainder of the molecule. See, e.g., Greene and Wuts, *Protective Groups in Organic Synthesis*, 2d ed, John Wiley & Sons, New York, 1991. The exocyclic amino groups can be protected, for example by treatment with benzoic anhydride, in a traditional solvent such as, for example, pyridine. Other suitable amine protecting groups include isobutyryl, phenoxyacetyl, and N2 phenoxyacetyl N6 dimethylformamidine.

2-halo-substituted aminoadenine nucleosides and nucleobases can be converted into their respective DMT/amidites following standard methods and techniques to give the 1-[5-O-dimethoxytrityl-2-O-substituted-(3-O-N,N-diisopropylamino-2-cyanoethylphosphite)]nucleoside, which can be used as a monomeric subunit precursor in the synthesis of oligomeric compounds using standard methods, such as phosphoramidite.

In the processes of the present invention, an oligonucleotide incorporating adenine heterocycles of formula (II) is reacted with an amine for conversion of the 2-halo substituent X to the group $NR_1R_2$ (and in particular by preferred embodiments, the 6-halo substituent Y). Representative amines include polyalkylamine ($NR_1R_2H$), aminoalkylamino, hydrazine ($NH_2$-$NHR_1R_2$), polyamines or hydroxylamine ($NH_2OR_1$). Most preferred is ammonium hydroxide.

Following deprotection of the oligonucleotide, $R_1$, $R_2$, $R_3$ and $R_4$ may be further conjugated using known methods. Examples of useful groups to be conjugated include cationic groups as disclosed in Manoharan, M., et al. (*Tetrahedron Lett.* 1996, 37, 7675–7678) targeting groups and intercalators. Conjugations of this nature may provide enhanced uptake properties.

Methods for synthesizing oligonucleotides include conversion to the phosphoramidite followed by solution phase or solid phase chemistries. Representative solution phase techniques are described in U.S. Pat. No. 5,210,264, issued May 11, 1993 and commonly assigned with this invention. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.)

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta,* 1995, 78, 486). It is also well known to use similar techniques and commercially available modified amidites and solid supports. Solid supports according to the invention include controlled pore glass (CPG)(available from Glen Research, Sterling, Va.), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene. Many other solid supports are commercially available and amenable to the present invention.

In the preparation of 2'-O-alkyl oligonucleotides, 2-aminoadenosine may be used as a common starting material for synthesis of 2'-O-alkyl guanosine derivatives and 2'-O-alkyl 2-aminoadenosine derivatives. Once 2-aminoadenosine is alkylated to make 2'-O-alkyl 2-aminoadenosine, some of this product can be treated, e.g., with adenosine deaminase to give 2'-O-alkyl guanosine (as disclosed in U.S. Pat. No. 5,506,351), or could be converted to 2'-O-alkyl 2-fluoro-adenosine (as described in this application) and subsequently used in the process of this invention. Thus, preparation of 2'-O-alkyl purine nucleosides can be achieved from a single intermediate source, and therefore at a lower cost.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates (usually abbreviated in the art as P=S) and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester (usually abbreviated in the art as P=O) backbone is represented as O—P—O—$CH_2$. Also preferred are oligonucleotides having morpholino backbone structures such as those of Summerton and Weller, U.S. Pat. No. 5,034,506.

Also preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide and thioamide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science*, 1991, 254, 1497; U.S. Pat. No. 5,539,082).

Other preferred modified oligonucleotides may contain one or more substituted sugar moieties comprising one of the following at the 2' position: OH, SH, $SCH_3$, F, OCN, $OCH_2CH_2OCH_3$, $OCH_2CH_2O(CH_2)_nCH_3$, $O(CH_2)_nNH_2$ or $O(CH_2)_nCH_3$ where n is from 1 to about 10; O—R or O—R—O—R where R is $C_1$ to $C_{10}$ lower alkyl, substituted lower alkyl, alkaryl or aralkyl; O-substituted lower alkyl, Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties.

Other substitutions at the 2' position include those disclosed in U.S. Ser. No. 09/016520, commonly assigned and herein incorporated by reference. Substitutions therein disclosed include aminooxy modifications, including O-aminooxyalkyl, O-alkylaminooxyalkyl and dialkylaminooxyethyl (e.g. dimethylaminooxyethyl) and are preferred. Another preferred modification includes 2'-O-methoxyethyl [which can be written as 2'—O—$CH_2CH_2OCH_3$, and is also known in the art as 2'-O-(2-methoxyethyl) or 2'-methoxyethoxy] (Martin, et al., *Helv. Chim. Acta* 1995, 78, 486). Other preferred modifications include 2'-methoxy (2'—O—$CH_3$), 2'-propoxy (2'—$OCH_2CH_2CH_3$) and 2'-fluoro (2'—F). Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonucleotides produced by this invention may additionally include other nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine and 5-methylcytosine, as well as synthetic nucleobases, e.g., 5-bromouracil, 5-hydroxymethyluracil, 8-azaguanines, 7-deazaguanine, $N^6$ (6-aminohexyl)adenine and 2,6-diaminopurine (Kornberg, A., *DNA Replication*, 1974, W.H. Freeman & Co., San Francisco, 1974, pp. 75–77; Gebeyehu, G., et al., *Nucleic Acids Res.* 1987, 15, 4513). 5-methylcytosine (5-me-C) is presently a preferred nucleobase, particularly in combination with 2'-O-methoxyethyl modifications.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine heterocycle may also be utilized to link a lipophilic moiety to an oligonucleotide of the invention (Gebeyehu, G., et al., *Nucleic Acids Res.* 1987, 15, 4513). Such lipophilic moieties include but are not limited to a cholesteryl moiety (Letsinger et al., *Proc. Natl. Acad. Sci. USA* 1989, 86, 6553), cholic acid (Manoharan et al., *Bioorg. Med. Chem. Let.* 1994, 4, 1053), a thioether, e.g., hexyl-S-tritylthiol (Manoharan et al., *Ann. N.Y. Acad. Sci.* 1992, 660, 306; Manoharan et al., *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al., 1991, *EMBO J.*, 10, 111; Kabanov et al., *FEBS Lett.* 1990, 259, 327; Svinarchuk et al., *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651; Shea et al., *Nucl. Acids Res.* 1990, 18, 3777), a polyamine or a polyethylene glycol chain (Manoharan et al., *Nucleosides & Nucleotides* 1995, 14, 969), or adamantane acetic acid (Manoharan et al., *Tetrahedron Lett.* 1995, 36, 3651), a palmityl moiety (Mishra et al., *Biochim. Biophys. Acta* 1995, 1264, 229), or an octadecylamine or hexylamino-carbonyl-oxycholesterol moiety (Crooke et al., *J. Pharmac ol. Exp. Ther.* 1996, 277, 923). Oligonucleotides comprising lipophilic moieties, and methods for preparing such oligonucleotides, as disclosed in U.S. Pat. No. 5,138,045, U.S. Pat. No. 5,218,105 and U.S. Pat. No. 5,459,255, the contents of which are hereby incorporated by reference.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art.

Examples of chimeric oligonucleotides include but are not limited to "gapmers," in which three distinct regions are present, normally with a central region flanked by two regions which may be chemically equivalent to each other but are distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted).

Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'—O—$CH_2CH_2OCH_3$) modification on the sugar moiety of at least one nucleotide. This modification has been shown to increase both affinity of the oligonucleotide for its target and nuclease resistance of the oligonucleotide.

According to certain embodiments of the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred. Oligonucleotides in accordance with this invention are from 5 to 50 nucleotides in length. In the context of this invention it is understood that this encompasses non-naturally occurring oligomers as hereinbefore described, having from 5 to 50 monomers.

Additional objects, advantages, and novel features of this invention will become apparent to those skilled in the art upon examination of the examples thereof provided below.

EXAMPLES

Examples 1–13 are depicted in Reaction scheme 1. Examples 14–20 are depicted in Reaction scheme 2. The underlined numbers in parentheses following the Example's title compound correspond to the compound numbers on the respective reaction schemes.

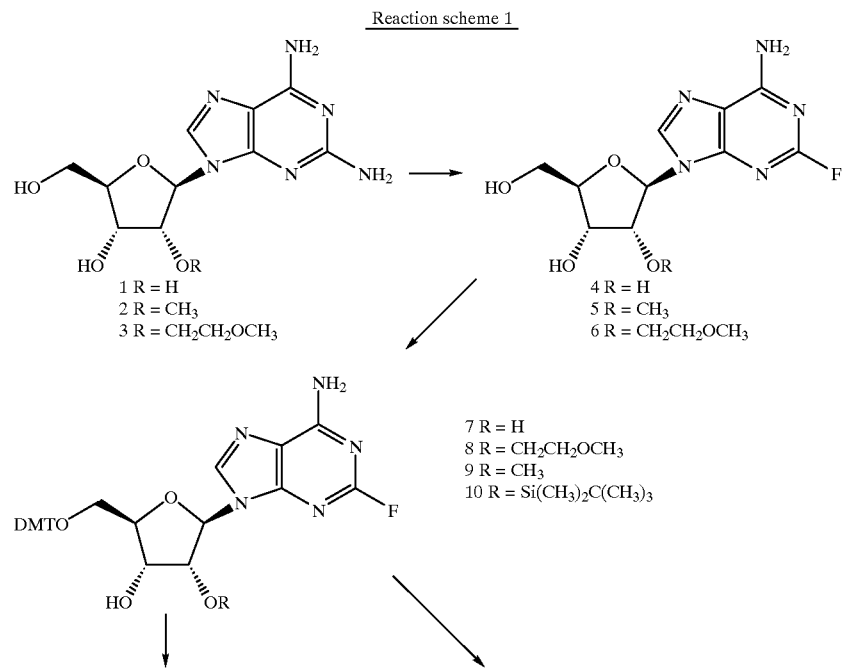

Reaction scheme 1

-continued

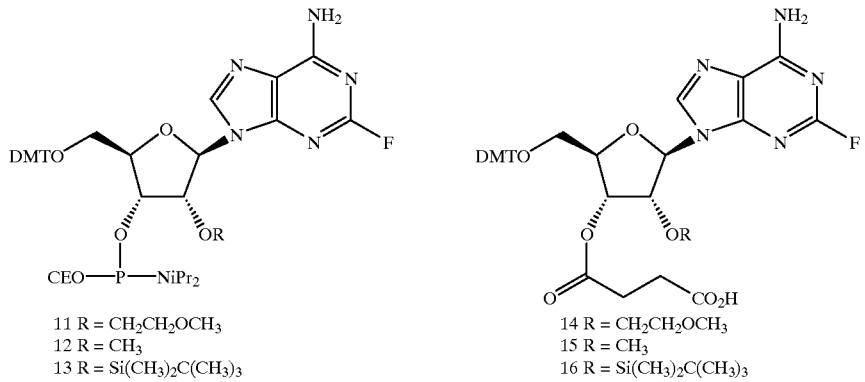

11 R = CH$_2$CH$_2$OCH$_3$
12 R = CH$_3$
13 R = Si(CH$_3$)$_2$C(CH$_3$)$_3$

14 R = CH$_2$CH$_2$OCH$_3$
15 R = CH$_3$
16 R = Si(CH$_3$)$_2$C(CH$_3$)$_3$

Reaction scheme 2

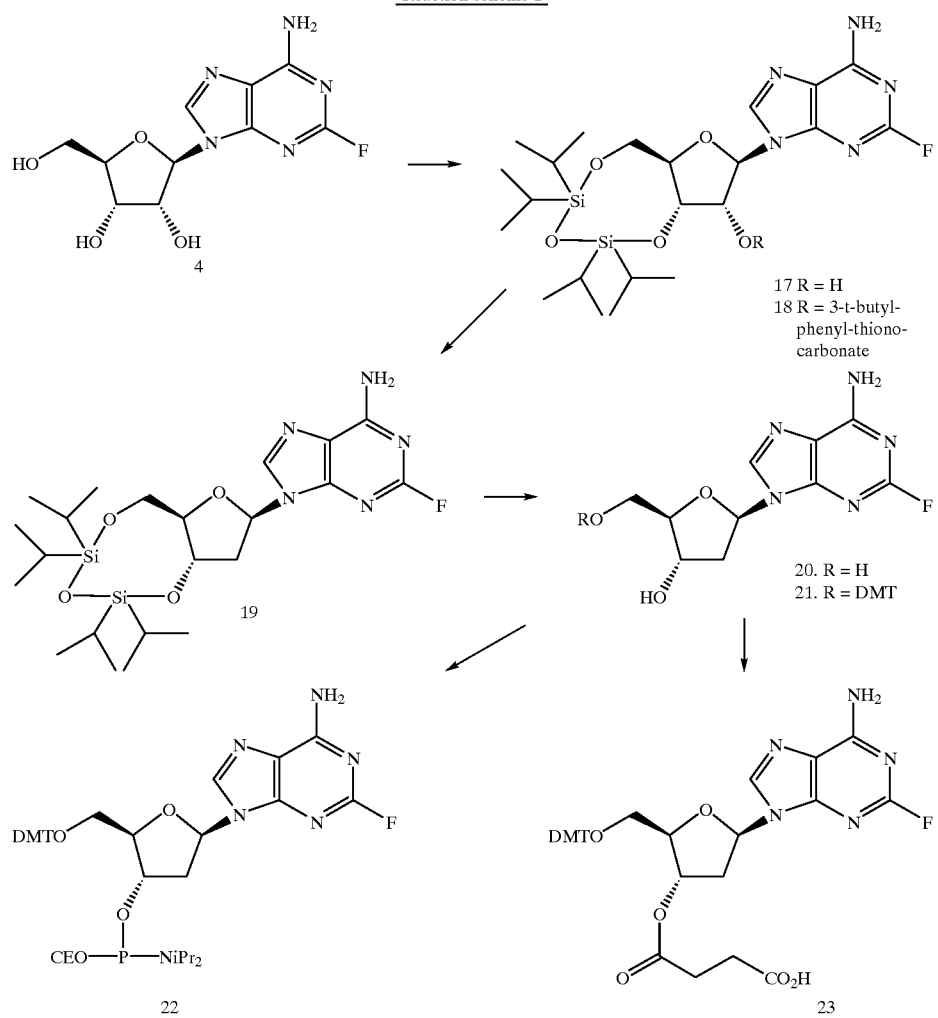

17 R = H
18 R = 3-t-butyl-phenyl-thiono-carbonate

20. R = H
21. R = DMT

Example 1

Preparation of 2-fluoroadenosine (4)

A 2 L polyethylene bottle was equipped with a magnetic stirrer, thermometer, dry ice/acetone bath and a stream of argon gas. Anhydrous pyridine (750 mL) was added and the solution was cooled to −20° C. To this was added 70% hydrogen fluoride in pyridine (500 mL). 2,6-diaminopurine riboside (1,2-aminoadenosine, 105 g, 0.372 mol, R.I. Chemical, Orange, Calif., Reliable Biopharmaceuticals, St.

Louis, Mo.) was suspended in the liquid. Tert-butylnitrite (90 mL, 0.76 mol) was added in one portion and the reaction was stirred at 9–11° C. until the reaction was complete as judged by TLC (3 h, Rf 0.20, starting material; Rf 0.40, product, ethyl acetate-methanol 4:1). Sodium bicarbonate (3 kg) was suspended with manual stirring in water (2 L) in a 20 L bucket. The reaction solution was slowly poured (to allow for evolution of carbon dioxide) into the aqueous layer with vigorous stirring. Ethyl acetate was added periodically in small portions to reduce foaming. The resulting suspension was extracted with ethyl acetate (5×1 L). The organic layers were combined and concentrated to a solid. The solid was mostly dissolved in warm methanol (300 mL). The solution was cooled in a ice water bath and the resulting solid was collected, rinsed with methanol (2×100 mL) and dried under vacuum (1 mm Hg, 25° C., 24 h) to give 76 g of product as a gold solid, mp 214–215° C. The mother liquor was concentrated to a solid and recrystallized from water (600 mL) to give in three crops an additional 18.3 g of similar quality product for a total of 90.3 g (85%). H-NMR (DMSO-d6) δ 3.4–3.8 (m, 2, 5' and 5"-H), 3.95 (m, 1, 4'-H), 4.14 (m, 1, 3'-H), 4.53 (m, 1, 2'-H), 5.04 (t, 1, 5'-OH), 5.23 (d, 1, 3'-OH), 5.50 (d, 1, 2'-OH), 5.80 (d, 1, 1'-H), 7.89 (br s, 2, $NH_2$), 8.37 (s, 1, 8-H).

Example 2

Preparation of 5'-O-(4,4'-dimethoxytriphenyliethyl)-2-fluoroadenosine (7)

2-Fluoroadenosine (4, 20.7 g, 0.0725 mol) and 4,4'-dimethoxytriphenylmethyl chloride (34.4g , 0.1016 mol) were dissolved in anhydrous pyridine (250 mL) at ambient temperature for 2 h. TLC (Rf 0.50, starting material; Rf 0.80, product, ethyl acetate-methanol 9:1) indicated only 80% conversion. An additional 7 g (0.021 mol) of the DMT chloride was added. TLC after 1 h indicated a complete reaction. The reaction was quenched by the addition of methanol (30 mL) and after 30 min, the reaction was concentrated under reduced pressure to an oil. The oil was partitioned between ethyl acetate (300 mL) and sat'd sodium bicarbonate solution (300 mL). The aqueous was extracted with more solvent (100 mL) and the combined organic layer was concentrated under reduced pressure to a small volume. A solid began to form. It was suspended in a mixture of hexanes-ethyl acetate (300 mL, 1:1) and then collected by filtration, washed with the same mix (3×150 mL) and dried (1 mm Hg, 25° C., 24 h) to 26.2 g of product as light yellow crystal, mp sh 139° C., melts 146–148 ° C. The combined filtrate was concentrated and purified by column chromatography (silica, 200 g) using a gradient of ethyl acetate in hexanes (70% to 80% to all ethyl acetate to 5% methanol in ethyl acetate). The appropriate fractions were combined, evaporated and dried as above to give 5.9 g more product as a foam for a total of 32.1 g (75.4%). H-NMR (DMSO-d6) δ 3.22 (m, 2, 5' and 5"-H), 3.75 (s, 6, O—$CH_3$), 4.08 (m, 1, 4'-H), 4.30 (dd, 1, 3'-H), 4.63 (dd, 1, 2'-H), 5.26 (d, 1, 3'-OH), 5.60 (d, 1, 2'-OH), 5.87 (d, 1, 1'-H), 6.87 (m, 4, arom.), 7.1–7.4 (m, 9, arom.), 7.92 (br s, 2, $NH_2$), 8.26 (s, 1, 8-H)

Example 3

Preparation of 2'-O-tert-butyl-dimethylsilyl-5'-O-(4, 4'-dimethoxytriphenylmethyl)-2-fluoroadenosine (10)

5'-O-(4,4'-dimethoxytriphenylmethyl)-2-fluoroadenosine (7, 14 g, 0.046 mol), tert-butyldimethylsilyl chloride (9.1 g, 0.060 mol), anhydrous pyridine (7.8 mL), silver nitrate (9.0 g, 0.053 mol) were dissolved in anhydrous tetrahydro-furan (125 mL). The reaction was stirred at ambient temperature under an argon atmosphere for 3 h. TLC indicated a complete reaction (Rf 0.10, starting material;, Rf 0.50, product, Rf 0.45, 3' isomer, hexanes-acetone 6:4). The reaction was quenched by the addition of water (25 ml) and then concentrated to an oil under reduced pressure. The residue was dissolved in a minimum of dichloromethane and applied onto a silica gel column (450 g) and eluted with hexanes-acetone (7:3). The appropriate fractions were combined, concentrated and then redissolved in a minimum of warm ethyl acetate to give a precipitate upon cooling. The solid was collected by filtration, washed with ethyl acetate (2×20 mL) and dried (1 mm Hg, 25° C., 24 h) to 8.5 g (50%) of product as white microcrystalline powder, mp 103–107° C. H-NMR (DMSO-d6) δ 0.0 (s, 6, Si—$CH_3$), 0.78 (s, 9, Si-t-but), 3.28 (m, 2, 5' and 5"-H), 3.74 (s, 6, O—$CH_3$), 4.09 (m, 1, 4'-H), 4.21 (dd, 1, 3'-H), 4.73 (dd, 1, 2'-H), 5.19 (d, 1, 3'-OH), 5.86 (d, 1, 1'-H), 6.85 (d, 4, arom.), 7.2–7.4 (m, 9, arom.), 7.90 (br s, 2, $NH_2$), 8.25 (s, 1, 8-H). F-NMR (DMSO-d6) δ-53.0 (s).

Example 4

Preparation of [5'-O-(4,4'-Dimethoxytritytl)-2'-O-tert-butyldimethylsilyl-2-fluoroadenosin-3'-O-yl]-N, N-diisopropylaminocyanoethoxy phosphoramidite (13)

5'-O-(4,4'-Dimethoxytrityl)-2'-O-tert-butyldimethylsilyl-2-fluoroadenosine (10, 5.0 g, 0.0071 mol), 2-cyanoethyl diisopropylchlorophosphoroamidite (5.6 mL, 0.025 mol), N-methyl imidazole (0.3 mL), collidine (7.2 mL) were dissolved in anhydrous tetrahydrofuran (75 mL) with stirring at ambient temperature under an argon atmosphere. After 2.5 h, TLC indicated a complete reaction (Rf 0.30, starting material; Rf 0.50 product diastereomers, hexanesacetone 6:4). The reaction was diluted with ethyl acetate (200 mL) and washed with sat'd sodium bicarbonate solution (300 mL). The aqueous layer was back-extracted with ethyl. acetate (75 mL). The combined organic layer was washed with brine (200 mL), concentrated under reduced pressure to a thin oil and then directly applied to a silica gel column (100 g). The product was eluted with a mixture of hexanes-acetone-triethylamine (70:29:1). The appropriate fractions were combined, concentrated under reduced pressure, coevaporated with anhydrous acetonitrile and dried (1 mm Hg, 25° C., 24 h) to 3.3 g (52%) of white foam. H-NMR ($CDCl_3$) δ 0.05 (d, 6, Si—$CH_3$), 0.82 (s, 9, Si-t-but), 1.0–1.4 (m, 14, N-iPr), 2.33 and 2.63 (t and t, 2, $CH_2CN$, diastereomers), 3.3–4.0 (m, 4, 5' and 5"-H and $CH_2CH_2CN$), 3.78 (s, 6, O—$CH_3$), 4.3–4.5 (m, 2, 3' and 4'-H), 4.90 (m, 1, 2'-H), 5.92 (dd 1, 1'-H), 6.50 (br s, 2, $NH_2$), 6.82 (m, 4, arom.), 7.2–7.5 (m, 9, arom.), 8.15 (d, 1, 8-H). F-NMR ($CDCl_3$) δ-51.6 (s). P-NMR ($CDCl_3$) δ 150.0 and 151.4 (s and s, diastereomers).

Example 5

Preparation of 5'-O-(4,4'-Dimethoxytrityl)-3'-O-succinyl-2'-O-tert-butyldimethylsilyl-2-fluoroadenosine (16)

5'-O-(4,4'-Dimethoxytrityl)-2'-O-tert-butyldimethylsilyl-2-fluoroadenosine (10, 1.0 g, 1.42 mmol), dimethylaminopyridine (0.32 g, 2.8 mmol) and succinic anhydride (0.87 g, 8.7 mmol) were dissolved in anhydrous pyridine (35 mL) and stirred at ambient temperature under an argon atmosphere until the reaction was complete (6 h) by TLC (Rf 0.50, starting material; Rf 0.17, product, ethyl acetate-hexanes 1:1). The reaction was quenched by the addition of water (10 mL) and then concentrated under reduced pressure to an oil. The oil was partitioned between ethyl acetate (200 mL) and sat'd sodium bicarbonate solution (200 mL). The aqueous layer was back extracted with more ethyl acetate. The combined organic phase was concentrated under reduced pressure and applied to a silica gel column (20 g). The product was eluted with a mix of ethyl acetate-hexanes (1:1). The appropriate fractions were combined, concentrated to a foam, coevaporated with acetonitrile (10 ml) and dried (1 mm Hg, 25° C., 24 h) to give product 0.70 9 (62%) as a white foam. H-NMR (DMSO-d6) δ-0.28 and 0.09 (s and s, 6, Si—$CH_3$, rotamers), 0.68 (s, 9, Si-t-but), 2.4–2.6 (m, 6, $CH_2CH_2$ $CO_2H$ and 5' and 5"-H), 3.74 (s, 6, O—$CH_3$), 4.22 (m, 1, 4'-H), 5.14 (dd, 1, 2'-H), 5.31 (dd, 1, 3'-H), 5.85 (d, 1, 1'-H), 6.86 (d, 4, arom.), 7.2–7.45 (m, 9, arom.), 7.95 (br s, 2, $NH_2$), 8.31 (s, 1, 8-H), 12.24 (br s, 1, $CO_2H$).

Example 6

Preparation of 2'-O-(2-methoxyethyl)-2-fluoroadenosine (6)

A 2 L polyethylene bottle was equipped with a magnetic stirrer, thermometer, dry ice/acetone bath and a stream of argon gas. Anhydrous pyridine (350 mL) was added and the solution was cooled to −20° C. To this was added 70% hydrogen fluoride in pyridine (200 mL) while maintaining the temperature below 0° C. 2'-O-(2-methoxyethyl)-2-aminoadenosine, (3, 42 g, 0.124 mol) was prepared as described in U.S. Pat. No. 5,506,351, herein incorporated by reference, using methyloxyethyl bromide (2-bromoethyl methyl ether) in place of either iodomethane or iodopropane. The product was dissolved in the solution. Tert-butylnitrite (56 mL, 0.47 mol) was added in one portion and the reaction was stirred at 5–16° C. until the reaction was complete as judged by TLC (2 h, Rf 0.40, starting material; Rf 0.60, product, ethyl acetate-methanol 6:4). Sodium bicarbonate (1400 g) was suspended with manual stirring in water (1.5 L) in a 20 L bucket. The reaction solution was slowly poured (to allow for evolution of carbon dioxide) into the aqueous layer with vigorous stirring. The resulting solution (pH 7 -8) was extracted with ethyl acetate (3×800 mL). The organic layers were combined and concentrated to an oil which was triturated with methanol (50 mL) to form a solid. The solid was collected by filtration and washed with ethyl acetate (3×50 mL) to 27.9 g of light tan crystals. The filtrate was concentrated under reduced pressure and redissolved in a minimum of methanol and allowed to stand at ambient temperature overnight. The second crop was collected as above to give 5.1 g. The mother liquor was concentrated again, then redissolved in a minimum of ethyl acetate and applied unto a silica gel column (100 g). The product was eluted with ethyl acetate. The appropriate fractions were combined and concentrated to 4.8 g of foam for a total of 37.8 g (89%) of product. A sample was recrystallized from methanol for elemental analysis to give white crystals, mp 152–154° C. Cd: C, 45.80, H, 5.28; N, 20.40. Fd: C, 45.48; H, 5.12; N, 20.20. H-NMR (DMSO-d6) δ 3.16 (s, 3, CH $_3OCH_2$) 3.35–3.75 (m, 6, 5' and 5"-H and $OCH_2CH_2O$), 3.97 (dd, 1, 4'-H), 4.31 (dd, 1, 3'-H), 4.48 (dd, 1, 2'-H), 5.12 (t, 1, 5'-OH), 5.18 (d, 1, 3'-OH), 5.91 (d, 1, 1'-H), 7.92 (br s, 2, $NH_2$), 8.39 (s, 1, 8-H).

Example 7

Preparation of 2'-O-(2-methoxyethyl)-5'-O-(4,4'-dimethoxytriphenylmethyl)-2-fluoroadenosine (8)

2'-O-(Methoxyethyl)-2-fluoroadenosine (6, 37.0 g, 0.108 mol) and 4,4'-dimethoxytriphenylmethyl chloride (40.2 g , 0.118 mol) were dissolved in anhydrous pyridine (250 mL) at ambient temperature for 1 h. TLC (Rf 0.50, starting material; Rf 0.80, product, ethyl acetate-methanol 4:1) indicated only 70% conversion. An additional 5 g (0.015 mol) of the DMT chloride was added. TLC after 1 h indicated a complete reaction. The reaction was quenched by the addition of methanol (30 mL) and after 30 min, the reaction was concentrated under reduced pressure to an oil. The oil was partitioned between ethyl acetate (300 mL) and sat'd sodium bicarbonate solution (300 mL). The aqueous was extracted with more solvent (300 mL) and the combined organic layer was concentrated under reduced pressure to a small volume and applied onto a silica gel column (700 g). The product was eluted with ethyl acetate-hexanes (9:1) and then ethyl acetate to obtain all the product. The appropriate pure fractions were combined, concentrated causing a precipitate to form. The product was dried (1 mm Hg, 25°0 C., 24 h) to 49.4 g yellow crystalline solid, mp 88–96° C. Impure fractions were combined and recolumned as above to give an additional 4.8 g for a total of 54.2 g (82%) as a light yellow foam. H-NMR (DMSO-d6) δ 3.18 (s, 3, CH $_3OCH_2$), 3.20–3.80 (m, 6, 5' and 5"-H and $OCH_2CH_2O$), 3.75 (s, 6, O—$CH_3$) 4.05 (m, 1, 4'-H), 4.40 (dd, 1, 3'-H), 4.59 (dd, 1, 2'-H), 5.22 (d, 1, 3'-OH), 5.95 (d, 1, 1'-H), 6.83 (m, 4, arom.), 7.15–7.4 (m, 9, arom.), 7.93 (br s, 2, $NH_2$), 8.27 (s, 1, 8-H). F-NMR (DMSO-d6) δ-52.8 (s).

Example 8

Preparation of [5'-O-(4,4'-Dimethoxytrityl)-2'-O-(2-methoxyethyl)-2-fluoroadenosin-3'-O-yl]-N,N-diisopropylaminocyanoethoxy phosphoramidite (11)

5'-O-(4,4'-Dimethoxytrityl)-2'-O-(2-methoxyethyl)-2-fluoroadenosine (8, 10 g, 0.16 mol), 2-cyanoethyl tetraisopropylphosphorodiamidite (6.9 g, 0.22 mol), diisopropylamine tetrazolide (0.84 g, 0.0049 mol) were dissolved in anhydrous dichloromethane (200 mL) and allowed to stir at ambient temperature under an argon atmosphere for 16 h. TLC indicated a complete reaction (Rf 0.20, starting material; Rf 0.55, product diastereomers, ethyl acetate-methanol 9:1). The reaction was washed with sat'd sodium bicarbonate solution. The aqueous layer was back-extracted with dichloromethane (100 mL). The combined organic layer was dried over sodium sulfate, concentrated to a thin oil and then directly applied to a silica gel column (200 9).

The product was eluted with ethyl acetate-hexanes-triethylamine (80:19:1). The appropriate fractions were combined, concentrated under reduced pressure, coevaporated with anhydrous acetonitrile and dried (1 mm Hg, 25° C., 24 h) to 9.3 g (70%) of product as a light yellow foam. H-NMR (CDCl$_3$) δ 1.0–1.3 (m, 14, N-iPr), 2.39 and 2.65 (t and t, 2, $CH_2CN$, diastereomers), 3.23 (s, 3, $CH_3O$-$CH_2$), 3.3–4.0 (m, 8, 5' and 5"-H and $CH_2CH_2CN$ and $OCH_2CH_2O$), 3.78 (s, 6, O—$CH_3$), 4.35 (m, 1, 4'-H), 4.60 (m, 1, 3'-H), 4.78 (m, 1, 2'-H), 5.90 (br s, 2, $NH_2$), 6.02 (dd, 1, 1'-H), 6.80 (m, 4, arom.), 7.2–7.5 (m, 9, arom.), 8.00 (d, 1, 8-H). P-NMR (CDCl$_3$) δ 150.7 and 151.0 (s and s, diastereomers).

Example 9

Preparation of 5'-O-(4,4'-Dimethoxytrityl)-3'-O-succinyl-2'-O-(2-methoxyethyl)-2-fluoroadenosine (14)

5'-O-(4,4'-Dimethoxytrityl)-2'-O-(2-methoxyethyl)-2-fluoroadenosine (8, 1.0 g, 1.63 mmol), dimethylaminopyridine (0.080 g, 0.66 mmol) and succinic anhydride (0.65 g, 6.5 mmol) were dissolved in anhydrous pyridine (10 mL) and stirred at ambient temperature under an argon atmosphere until the reaction was complete (6 h) by TLC (Rf 0.60, starting material; Rf 0.40, product, ethyl acetate-methanol 6:4). The reaction was quenched by the addition of water (10 mL) and then concentrated under reduced pressure to an oil. The oil was partitioned between ethyl acetate (75 mL) and 20% aqueous citric acid (75 mL). The organic phase was washed with water (2×75 mL), dried over sodium sulfate, concentrated under reduced pressure, coevaporated with acetonitrile (100 mL) and dried (1 mm Hg, 25° C., 24 h) to 1.0 g (83%) of product as a white foam. H-NMR (DMSO-d6) δ 2.4–2.6 (m, 4, $CH_2CH_2CO_2H$), 3.55 (m, 2, 5' and 5"-H), 3.75 (s, 6, O—$CH_3$), 4.22 (m, 1, 4'-H), 4.98 (dd, 1, 2'-H), 5.42 (dd, 1, 3'-H), 5.95 (d, 1, 1'-H), 6.84 (m, 4, arom.), 7.2–7.45 (m, 9, arom.), 7.97 (br s, 2, $NH_2$), 8.32 (s, 1, 8-H), 12.23 (br S, 1, $CO_2H$).

Example 10

Preparation of 2'-O-methyl-2-fluoroadenosine (5)

A 2 L polyethylene bottle was equipped with a magnetic stirrer, thermometer, dry ice/acetone bath and a stream of argon gas. Anhydrous pyridine (200 mL) was added and the solution was cooled to $-20°$ C. To this was added 70% hydrogen fluoride in pyridine (100 mL) while maintaining the temperature below 0° C. 2'-O-Methyl-2-aminoadenosine, (2, 30 g, 0.101 mol, R.I. Chemical, Orange, Calif., Reliable Bio-pharmaceuticals, St. Louis, Mo.) was dissolved in the solution. Tert-butylnitrite (42 mL, 0.35 mol) was added in one portion and the reaction was stirred at 5–13° C. until the reaction was complete as judged by TLC (2 h, Rf 0.15, starting material; Rf 0.28, product, ethyl acetate-methanol 9:1). Sodium bicarbonate (600 g) was suspended with manual stirring in water (1 L) in a 20 L bucket. The reaction solution was slowly poured (to allow for evolution of carbon dioxide) into the aqueous layer with vigorous stirring. The resulting solution (pH 7–8) was extracted with ethyl acetate (5×400 mL). The organic layers were combined and concentrated to an oil which was triturated with methanol (70 mL) to form a solid. The solid was collected by filtration and washed with ethyl acetate (3×50 mL) and dried (1 mm Hg, 25° C., 24 h) to 16.5 g of product as a cream colored microcrystalline solid, mp 239–241° C. The filtrate was concentrated under reduced pressure to about half volume and a second crop was collected as above to give as additional 1.0 g or 17.5 g total (58%). More product remained in the mother liquor. H-NMR (DMSO-d6) δ 3.36 (s, 3, 2'—O—$CH_3$) 3.50–3.75 (m, 2, 5' and 5"-H), 3.98 (m, 1, 4'-H), 4.32 (m, 2, 3'-H and 2'-H), 5.14 (t, 1, 5'-OH), 5.31 (d, 1, 3'-OH), 5.92 (d, 1, 1'-H), 7.92 (br s, 2, $NH_2$) 8.40 (s, 1, 8-H).

Example 11

Preparation of 2'-O-Methyl-5'-O-(4,4'-dimethoxy triphenylmethyl)-2-fluoroadenosine (9)

2'-O-Methyl-2-fluoroadenosine (5, 16.5 g, 0.055 mol) and 4,4'-dimethoxytriphenylmethyl chloride (24.3 g, 0.0717 mol) were dissolved in anhydrous pyridine (150 mL) at ambient temperature for 1 h. TLC (Rf 0.30, starting material; Rf 0.60, product, ethyl acetate-methanol 9:1) indicated only 70% conversion. An additional 10 g (0.030 mol) of the DMT chloride was added. TLC after 1 h indicated a complete reaction. The reaction was quenched by the addition of methanol (50 mL) and after 30 min, the reaction was concentrated under reduced pressure to an oil. The oil was taken up in ethyl acetate (50 mL) and adsorbed onto silica gel (60 g). The silica was dried under reduced pressure to a free flowing powder and placed on top of a silica gel column (200 g). The product was eluted with FL gradient of ethyl acetate in hexanes (50% to 100% ethyl acetate). The appropriate fractions were combined, concentrated and dried (1 mm Hg, 25° C., 24 h) to 19.1 g (58%) of product as a yellow foam. H-NMR (DMSO-d6) δ 3.22 (m, 2, 5'-H and 5"-H), 3.38 (s, 3, 2'—O—$CH_3$), 3.75 (s, 6, O—$CH_3$), 4.05 (m, 1, 4'-H), 4.41 (m, 2, 2'-H and 3'-H), 5.31 (d, 1, 3'-OH), 5.97 (d, 1, 1'-H), 6.83 (m, 4, arom.), 7.15–7.4 (m, 9, arom.), 7.93 (br s, 2, $NH_2$), 8.25 (s, 1, 8-H). F-NMR (DMSO-d6) δ-52.8 (s).

Example 12

Preparation of [5'-O-(4,4'-Dimethoxytrityl)-2'-O-methyl-2-fluoroadenosin-3'-O-yl]-N,N-diisopropylaminocyanoethoxy phosphoramidite (12)

5'-O-(4,4'-Dimethoxytrityl)-2'-O-methyl-2-fluoroadenosine (9, 10 g, 0.17 mol), 2-cyanoethyl tetra-isopropylphosphorodiamidite (7.0 g, 0.23 mol), diisopropylamine tetrazolide (0.85 g, 0.0050 mol) were dissolved in anhydrous dichloromethane (100 mL) and allowed to stir at ambient temperature under an argon atmosphere for 16 h. TLC indicated a complete reaction (Rf 0.40, starting material; Rf 0.65 and 0.70, product diastereomers, ethyl acetate). With no workup, the reaction was added directly to a silica gel column (200 g) and eluted with a mixture of ethyl acetate-hexanes-triethylamine (60:39:1). The product containing fractions were combined and concentrated to 10.2 g of foam. P-NMR indicated an 8- impurity peak at 7 ppm. The product was recolumned using ethyl acetate-triethylamine (99:1) to give 8 g of pure product and 2 g of 30% impure product which was discarded. The pure product was coevaporated with acetonitrile (50 mL) and dried (1 mm Hg, 25° C., 24 h) to 7.5 g (56%) of product as white foam. H-NMR ($CDCl_3$) d 1.0–1.3 (m, 14, N-iPr), 2.37 and 2.66 (t and t, 2, $CH_2CN$, diastereomers), 3.2–4.0 (m, 4, 5' and 5"-H and $CH_2CH_2CN$), 3.49 (s, 3, 2'-O-$CH_3$), 3.78 (s, 6, O—$CH_3$), 4.3–4.7 (m, 3, 2'-H, 3'-H and 4'-H), 6.02 (dd, 1, 1'-H), 6.51 (br s, 2, $NH_2$), 6.82 (m, 4, arom.), 7.2–7.5 (m, 9, arom.), 7.98 (d, 1, 8-H). P-NMR ($CDCl_3$) δ 150.9 and 151.5 (s and s, diastereomers). F-NMR ($CDCl_3$) δ-51.7 (s).

Example 13

Preparation of 5'-O-(4,4'-Dimethoxytrityl)-3'-O-succinyl-2'-O-methyl-2-fluoroadenosine (15)

5'-O-(4,4'-Dimethoxytrityl)-2'-O-methyl-2-fluoro-adenosine (9, 2.0 g, 3.32 mmol), dimethylaminopyridine (0.81 g, 6.6 mmol) and succinic anhydride (1.3 g, 13.3 mmol) were dissolved in anhydrous pyridine (10 mL) and stirred at ambient temperature under an argon atmosphere until the reaction was complete (2 h) by TLC (Rf 0.90, starting material; Rf 0.30, product, ethyl acetate-methanol 6:4). The reaction was quenched by the addition of water (30 mL) and then concentrated under reduced pressure to an oil. The oil was partitioned between ethyl acetate (100 mL) and 20% aqueous citric acid (100 mL). The organic phase was washed with water (2×100 mL), dried over sodium sulfate, concentrated under reduced pressure. TLC indicated impurities so the product was dissolved in a minimum of ethyl acetate, applied on a silica gel column (30 g) and washed with ethyl acetate-methanol (95:5) and then eluted with ethyl acetate-methanol (6:4). The product containing fractions were combined, concentrated under reduced pressure, coevaporated with acetonitrile (20 mL) and triethylamine (5 mL) and dried (1 mm Hg, 25° C., 24 h) to 2.1. g (90%) of the triethylamine salt of the product as a white foam. H-NMR (DMSO-d6) δ 0.96 (t, 9, $CH_3CH_2N$), 2.4–255 (m, 10, $CH_2CH_2CO_2H$ and $NCH_2CH_3$), 3.26 (s, 3, 2'—O—$CH_3$), 3.40 (m, 2, 5' and 5"-H), 3.74 (s, 6, O—$CH_3$), 4.22 (m, 1, 4'-H), 4.82 (dd, 1, 2'-H), 5.42 (dd, 1, 3'-H), 5.96 (d, 1, 1'-H), 6.83 (m, 4, arom.), 7.2–7.45 (m, 9, arom.), 7.95 (br s, 2, $NH_2$).

Example 14

Preparation of 3',5'-O-(1,1,3,3-Tetraisopropyl-1,3-disiloxanediyl-2-fluoroadenosine (17)

2-Fluoroadenosine (4, 22.5 g, 0.0789 mol) and 1,3-dichloro-(1,1,3,3-tetraisopropyl-1,3-disiloxane (28.8 g, 0.913 mol) were dissolved in anhydrous pyridine (150 mL) and stirred under an argon atmosphere at ambient temperature until the reaction was complete (3 h) by TLC (Rf 0.05, starting material; Rf 0.25, product; hexanes-ethyl acetate 1:1). The reaction was quenched with methanol (50 mL). After 20 min, the reaction was concentrated under reduced pressure to an oil which in turn was partitioned between ethyl acetate (400 mL) and a sat'd sodium bicarbonate solution (500 mL). The aqueous layer was extracted with more ethyl acetate (200 mL). The organic layers were combined, concentrated under reduced pressure and the resulting oil was applied onto a silica gel column (1.5 kg). The column was eluted with ethyl acetate until the product started to appear and then the polarity was increased by the addition of 5% methanol to drive off the balance of the product. The appropriate fraction were combined, concentrated under reduced pressure and dried (1 mm Hg, 25° C., 24 h) to a foam, 62 g which was still heavily contaminated with silyl reagent (theory 39.6 g). NMR was consistent with structure and this material was used as is in the next step.

Example 15

Preparation of 3',5'-O-(1,1,3,3-Tetralsopropyl-1,3-disiloxanediyl)-2'-O-(3-tert-butylphenylthionocarbonyl)-2-fluoroadenosine (18)

3',5'-O-(1,1,3,3-Tetraisopropyl-1,3-disiloxanediyl-2-fluoroadenosine (17, crude 62 g, theory 39.6 g, 0.79 mol), 3-tert-butylphenyl chlorothionoformate (22.6 g, 0.10 mol) dimethylaminopyridine (15.4 g, 0.126 mol) were dissolved in anhydrous dichloromethane (500 mL). The reaction was allowed to stir under an argon atmosphere at ambient temperature until complete (2 h) by TLC (Rf 0.25, starting material; Rf 0.50, product; hexanes-ethyl acetate 1:1). The reaction was quenched by the addition of a sat'd sodium bicarbonate solution (450 mL). The layers were separated and the aqueous layer was extracted with more dichloromethane (200 mL). The combined organic layers were concentrated under reduced pressure to an oil which in turn was redissolved in a minimum of ethyl acetate. A crystalline precipitate formed. This was collected, washed with ethyl acetate (2×100 mL) and dried (1 mm Hg, 25° C., 24 h) to a white solid, 25.2 g, mp 226–228° C. The mother liquor was concentrated and the resulting oil was purified by silica gel chromatography (hexanes-ethyl acetate, 7::3) to give another 10.6 g of product as a foam. The combined product weighed 35.8 g (64% two-step yield). H-NMR (DMSO-d6) δ 1.05 (m, 28, Si-iPr), 1.30 (s, 9, t-butyl), 3.9–4.1 (m, 4, 3'-H, 4'-H, 5' and 5"-H), 5.37 (dd, 1, 2'-H), 6.36 (s, 1, 1'-H), 6.43 (d, 1, 3'-OH), 6.95–7.5 (m, 4, arom.), 7.98 (br s, 2, $NH_2$), 8.28 (s, 1, 8-H).

Example 16

Preparation of 3',5'-O-(1,1,3,3-Tetraisopropyl-1,3-disiloxanediyl)-2'-deoxy-2-fluoroadenosine (19)

3',5'-O-(1,1,3,3-Tetraisopropyl-1,3-disiloxanediyl)-2'-O-(3-tert-butylphenylthionocarbonyl)-2-fluoroadenosine (18, 35.7 g, 0.50 mol) was dissolved in toluene (600 mL). Tributyltin hydride (28 g, 0.96 mol) and AIBN (2,2'-azobisisobutyronitrile, 7.6 g, 0.046 mol) were added and the solution was heated to reflux with stirring for 30 min. TLC indicated a complete reaction (Rf 0.50, starting material; Rf 0.35, product; hexanes-ethyl acetate 1:1). The reaction was allowed to cool and then it was diluted with methanol (100 mL). The solution was concentrated under reduced pressure to an oil which in turn was applied onto a silica gel column (700 g) and eluted with hexanes and then a mixture of hexanes-ethyl acetate (7:3). The product containing fractions were combined, concentrated under reduced pressure to a solid paste which in turn was triturated with hexanes (300 mL), collected, dried (1 mm Hg, 25° C., 24 h) to 20.8 g of product as a white small crystals, mp 201–202° C. The filtrate was concentrated and recoluuned to give an additional 1.5 g of similar material for a total of 22.3 g (86.5%). H-NMR (DMSO-d6) δ 1.05 (m, 28, Si-iPr), 2.5–2.9 (m, 2, 2'-$CH_2$), 3.6–3.9 (m, 4, 3'-H, 4'-H, 5' and 5"-H), 5.12 (dd, 1, 3'-H), 6.22 (dd, 1, 1'-H), 7.83 (br s, 2, $NH_2$), 8.22 (s, 1, 8-H).

Example 17

Preparation of 2'-deoxy-2-fluoroadenosine (20)

3',5'-O-(1,1,3,3-Tetraisopropyl-1,3-disiloxanediyl)-2'-deoxy-2-fluoroadenosine (19, 22.2 g, 0.46 mol) was dissolved in anhydrous tetrahydrofuran (150 mL). Triethylamine (10 mL, 0.72 mol) and triethylamine trihydrofluoride (20 mL, 0.122 mol) were added and the reaction was stirred at ambient temperature until the reaction was complete (3 h) by TLC (Rf 0.90, starting material; Rf 0.20, product; ethyl acetate-methanol 9:1). The reaction was concentrated under reduced pressure to an oily solid. The residue was redissolved in a minimum of methanol and stirred with Dowex-50 beads (sulfonic acid resin, H+ form, 150 g of dry weight). The solution was filtered, concentrated to an oil and applied to a silica gel column (400 g). The product was eluted with a gradient of methanol in ethyl acetate (0–20%). The appropriate fractions were combined, concentrated under reduced pressure and dried (1 mm Hg, 25° C., 24 h) to a solid, 12.1 g (98%), mp darkens above 178° C. but melts above 250° C. H-NMR (DMSO-d6) δ 2.2–2.3 and 2.6–2.75 (m, 2, 2'-$CH_2$), 3.4–3.7 (m, 2, 5' and 5"-H), 3.85 (m, 1, 4'-H), 4.40 (m, 1, 3'-H), 4.98 (t, 1, 5'-OH), 5.35 (d, 1, 3'-OH), 6.23 (t, 1, 1'-H), 7.83 (br s, 2, $NH_2$), 8.34 (s, 1, 8-H)

Example 18

Preparation of 5'-O-(4,4'-Dimethoxytrityl)-2'-deoxy-2-fluoroadenosine (21)

2'-deoxy-2-fluoroadenosine (20, 12 g, 0.45 mol) and dimethoxytrityl chloride (18.1 g, 0.53 mol) were dissolved in anhydrous pyridine (100 mL) and stirred at ambient temperature until the trace amount of the starting material remaining matched the bis DMT impurity forming (3 h) as monitored by TLC (Rf 0.20, starting material; Rf 0.60, product; Rf 0.85, bis DMT product, ethyl acetate-methanol 9:1). The reaction was quenched by the addition of methanol (50 mL) and then concentrated under reduced pressure to an oil. The residue was partitioned between ethyl acetate (250 mL) and sat'd sodium bicarbonate (250 mL). The aqueous layer was extracted with ethyl acetate (100 mL) once more and the combined extracts were concentrated under reduced pressure. The resulting oil was purified by silica gel chromatography (400 g) using a gradient of methanol in ethyl acetate (0–5%). The appropriate fractions were combined, concentrated under reduced pressure, coevaporated with anhydrous acetonitrile (200 mL) and dried (1 mm Hg, 25° C., 24 h) to a foam, 23.2 g (90%). The product can be crystallized from dichloromethane to give white crystals, mp 239–243° C. H-NMR (DMSO-d6) d 2.2–2.4 and 2.7–2.9 (m, 2, 2'-$CH_2$), 3.18 (m, 2, 5'-H and 5"-H), 3.75 (s, 6, O—$CH_3$), 3.98 (m, 1, 4'-H), 4.43 (m, 1, 3'-H), 5.38 (d, 1, 3'-OH), 6.15 (t, 1, 1'-H), 6.83 (m, 4, arom.), 7.15–7.4 (m, 9, arom.), 7.83 (br s, 2, $NH_2$), 8.23 (s, 1, 8-H). F-NMR (DMSO-d6) δ-53.5 (s).

Example 19

Preparation of [5'-O-(4,4'-Dimethoxytrityl)-2'-deoxy-2-fluoroadenosin-3'-O-yl]-N,N-diisopropylamino cyanoethoxy phosphoramidite (22)

5'-O-(4,4'-Dimethoxytrityl)-2'-deoxy-2-fluoroadenosine (21, 10 g, 0.18 mol), 2-cyanoethyl tetraisopropyl phosphorodiamidite (7.6 g, 0.25 mol), diisopropylamine tetrazolide (0.93 g, 0.0054 mol) were dissolved in anhydrous dichloromethane (100 mL) and allowed to stir at ambient temperature under an argon atmosphere for 16 h. TLC indicated a complete reaction (Rf 0.30, starting material; Rf 0.60 and 0.65, product diastereomers, ethyl acetate). The reaction was concentrated under reduced pressure to a thin oil and then directly applied to a silica gel column (200 g). The product was eluted with ethyl acetate-triethylamine (99:1). The appropriate fractions were combined, concentrated under reduced pressure, coevaporated with anhydrous acetonitrile and dried (1 mm Hg, 25° C., 24 h) to 9.8 g (73%) of white foam. H-NMR (CDCl$_3$) d 1.0–1.3 (m, 14, N-iPr), 2.45 and 2.63 (t and t, 2, CH$_2$CN, diastereomers), 2.80 (m, 2, 2'-CH$_2$), 3.3–4.0 (m, 4, 5' and 5"-H and CH$_2$CH$_2$CN), 3.78 (s, 6, O—CH$_3$), 4.25 (m, 1, 4'-H), 4.77 (m, 1, 3'-H), 6.36 (dd, 1, 1'-H), 6.50 (br s, 2, NH$_2$), 6.82 (m, 4, arom.), 7.2–7.5 (m, 9, arom.), 7.98 (d, 1, 8-H). P-NMR (CDCl$_3$) δ 149.5 (s, diastereomers don't resolve).

Example 20

Preparation of 5'-O-(4,4'-Dimethoxytrityl)-3'-O-succinyl-2'-deoxy-2-fluoroadenosine (23)

5'-O-(4,4'-Dimethoxytrityl)-2'-deoxy-2-fluoroadenosine (21, 2.3 g, 4.03 mmol), dimethylaminopyridine (0.16 g, 1.3 mmol) and succinic anhydride (1.7 g, 17 mmol) were dissolved in anhydrous pyridine (20 mL) and stirred at ambient temperature under an argon atmosphere until the reaction was complete (6 h) by TLC (Rf 0.80, starting material; Rf 0.20, product, ethyl acetate-methanol 4:1). The reaction was quenched by the addition of water (20 mL) and then concentrated under reduced pressure to an oil. The oil was partitioned between ethyl acetate (100 mL) and 20% aqueous citric acid (100 mL). The organic phase was washed with water (2×100 mL), dried over sodium sulfate, concentrated under reduced pressure to an oil. The oil was redissolved in a minimum of dichloromethane (10 mL) and added with vigorous stirring to hexanes (100 mL) to give a precipitate. This was collected by filtration, washed with hexanes (3×50 mL,) and dried (1 mm Hg, 25° C., 24 h) to 1.8 g (58%) of product as a white solid. H-NMR (DMSO-d6) δ 2.4–2.65 (m, 6, CH$_2$CH$_2$CO$_2$H and 2'-CH$_2$), 3.0–3.4 ( m, 2, 5' and 5"-H), 3.74 (s, 6, O—CH$_3$), 4.18 (m, 1, 4'-H), 5.37 (m, 1, 3'-H), 6.30 (dd, 1, 1'-H), 6.81 (m, 4, arom.), 7.2–7.45 (m, 9, arom.), 7.92 (br s, 2, NH$_2$), 8.25 (s, 1, 8-H), 12.32 (br s, 1, CO$_2$H).

Example 21

Oligonucleotide synthesis

Oligonucleotides were synthesized on a Perseptive Biosystems Expedite 8901 Nucleic Acid Synthesis System. multiple 1-μmol syntheses were performed for each oligonucleotide. During a chain elongation, trityl groups were removed with trichloroacetic acid (975 μL over one minute) followed by an acetonitrile wash.

Phosphodiester protocol—All standard amidites (0.1M) were coupled over a 1.5 minute time frame, delivering 105 μL material. All novel amidites were dissolved in dry acetonitrile (100 mg of amidite/1 mL acetonitrile) to give approximately 0.08–0.1 M solutions. Total coupling time was approximately 5 minutes (210 μL of amidite delivered). 1-H-tetrazole in acetonitrile was used as the activating agent. Excess amidite was washed away with acetonitrile. (1S)-(+)-(10-camphorsulfonyl) oxaziridine (CSO, 1.0 g CSO/ 8.72 ml dry acetonitrile) was used to oxidize (3 minute wait step) delivering approximately 375 μL of oxidizer.

Thioate protocol—Standard amidites were delivered (210 μL) over a 3 minute period in this protocol. The novel amidites were double coupled using 210 μL over a total of 13 minutes. The amount of oxidizer, 3H-1,2-benzodithiole-3-one-1,1-dioxide (Beaucage reagent, 3.4 g Beaucage reagent/200 mL acetonitrile), was 225 μL (one minute wait step). In both protocols, unreacted functionalities were capped with a 50:50 mixture of tetrahyrdofuran/acetic anhydride and tetrahydrofuran/pyridine/1-methyl imidazole. Trityl yields were followed by the trityl monitor during the duration of the synthesis. The final DMT group was left intact. Following completion of the chain assembly, the oligonucleotide was cleaved from the CPG cartridge at 55° C. using 30% NH$_4$OH (1 mL for 1 μmol columns) for approximately 16 hours.

Example 22

Oligonucleotide Purification

After the deprotection step, the samples were filtered from CPG using Gelman 0.45 μm nylon acrodisc syringe filters. Excess NH$_4$OH was evaporated away in a Savant AS160 automatic speed vac. The crude yield was measured on a Hewlett Packard 8452A Diode Array Spectrophotometer at 260 nm. Crude samples were then analyzed by mass spectrometry (MS) on a Hewlett Packard electrospray mass spectrometer. Trityl-on oligonucleotides were purified by reverse phase preparative high performance liquid chromatography (HPLC). HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; Gradient: 5% B for first five minutes with linear increase in B to 60% during the next 55 minutes. Fractions containing the desired product were collected and the solvent was dried off in the speed vac. Oligonucleotides were detritylated in 80% acetic acid for approximately 60 minutes and lyophilized again. Free trityl and excess salt were removed by passing detritylated oligonucleotides through Sephadex G-25 (size exclusion chromatography) and collecting appropriate samples through a Pharmacia fraction collector. The solvent was again evaporated away in a speed vac. Purified oligonucleotides were then analyzed for purity by CGE, HPLC (flow rate: 1.5 mL/min; Waters Delta Pak C4 column, 3.9×300 mm), and MS. The final yield was determined by spectrophotometer at 260 nm. All samples for NMR analysis were passed through a Dowex column (in exchange of Et$_3$NH$^+$ to Na$^+$) followed by a Chelex column.

Example 23

Oligonucleotide Sequences

Oligonucleotides synthesized are listed in Table 1.
Mass spectrometry 0.5 OD of oligo in an approximately 50 isopropanol:50 water mix (total volume of 100 mL including 2.5 mL 100 mM piperidine) was analyzed by mass spectrometry (Hewlett Packard 59987A Series II API 5989A electrospray mass spectrometer). The purified 0.5 OD sample was first desalted by osmosis on a Millipore filter (filter type VS with 0.025 mM pore size) for one hour. (Water with 10 drops of 28.0–30% NH4OH were added to a petri dish. The 0.5 OD oligo sample was placed on the filter, floating on the water, for approximately one hour.)

Purified yields were quantitated using a Hewlett Packard 8452A Diode Array Spectrophotometer at 260 nm. Results are shown in Table 2. All oligonucleotides synthesized gave the expected molecular weights.

TABLE I

Oligonucleotides containing 2-aminoadenosine

| ISIS # | SEQ ID | Sequence (5'-3'): An asterisk indicates 2-aminoadenosine; underlined is 2'-methoxyethyl; and italicized cytosines are 5-methyl. | Back bone | Chemistry |
|---|---|---|---|---|
| 17236-2 | 1 | <u>A*TG-CA*T</u>-TCT-GCC-CC<u>C-A*A*G-GA</u> | P=S | 2'-O-MOE & 2'-H |
| 24695 | | GTCA* | P=S | 2'-H |
| 24681 | 2 | T*CC* GT*C* A\*T*C* GCT *CCT* C*A*\*G GG | P=S | 2'-H |
| 24682 | 3 | G*CC* C*A***A* GCT GG*C* A\*T*C* CGT C*A** | P=S | 2'-H |
| 24683 | 4 | GTT *CTC* GCT GGT GA\*G TTT C*A** | P=S | 2'-H |
| 24684 | 5 | T*CC* *CGC* *CTG* TG**A*\**CA*\*TG*C**A*\*TT | P=S | 2'-H |
| 24685 | | GA\*CT | P=O | 2'-H |
| 24701 | 6 | GGA\**CCG* GA\*b A\* GGT A\**CG* A\*G | P=O | 2'-H |
| 24702 | 7 | *CTC* GT**A* CCA*\* TT*C* *CGG* T*CC* | P=O | 2'-H |
| 24703 | 8 | A\**CC* GA\*G GA\*T CA\*T GT*C* GT**A*\* *CGC* | P=O | 2'-H |

TABLE II

Physical characteristics of Oligonucleotide incorporating 2-aminoadenosine

| ISIS # | SEQ ID | Sequence (5'-3') An asterisk indicates 2-amino-adenosine; underlined is 2'-methoxyethyl; and italicized cytosines are 5-methyl. | Expected Mass (g) | Observed Mass (g) | HPLC Retn. Time (min.) | ODs @ 260 nm Purified |
|---|---|---|---|---|---|---|
| 17236-2 | 1 | <u>A*TG-CA*T</u>-TCT-GCC-CC<u>C-A*A*G-GA</u> | 7344 | 7344 | | 194 |
| 24695 | | GTCA* | 1237 | 1236 | 19.4 | 48 |
| 24681 | 2 | TCC GTC A*TC GCT CCT CA*G GG | 6495 | 6491 | 21.5 | 56 |
| 24682 | 3 | GCC CA*A* GCT GGC A*TC CGT CA* | 6540 | 6539 | 22.6 | 140 |
| 24683 | 4 | GTT CTC GCT GGT GA*G TTT CA* | 6521 | 6521 | 21.8 | 105 |
| 24684 | 5 | TCC CGC CTG TGA*CA*TGCA*TT | 6492 | 6493 | 22.1 | 105 |
| 24701 | 6 | GGA*CCG GA*A* GGT A*CG A*G | 5385 | 5384 | | 27 |
| 24702 | 7 | CTC GTA CCA* TTC CGG TCC | 5402 | 5400 | 18.0 | 45 |
| 24703 | 8 | A*CC GA*G GA*T CA*T GTC GTA* CGC | 6506 | 6504 | 16.4 | 421 |

What is claimed is:

1. A process for preparing an oligonucleotide comprising a nucleoside with a 2,6-disubstituted purine heterocycle having formula (I)

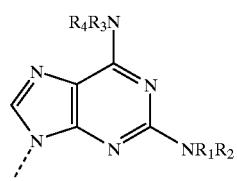

(I)

wherein
$R_1$, $R_2$, $R_3$ and $R_4$ are, independently, H or a unsubstituted or substituted hydrocarbyl group having from 1 to about 30 carbon atoms, or $R_1$ and $R_2$ form a 5 to 13 membered ring or ring system optionally incorporating additional heteroatoms selected from N, O and S, or $R_3$ and $R_4$ form a 5 to 13 membered ring or ring system optionally incorporating one or more additional heteroatoms selected from N, O and S; comprising:

reacting an oligonucleotide comprising a nucleoside with a 2-halo 6-substituted purine heterocycle having formula (II)

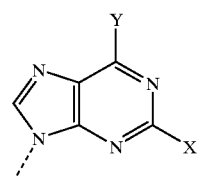

(II)

wherein
X is halogen;
Y is F, Cl, Br, I, $NR_3R_4$, or $NR_3Pg$; and
Pg is a protecting group;

with an amine under conditions to convert the 2-halo 6-substituted purine heterocycle of formula (II) to a heterocycle of formula (I).

2. The process of claim 1, wherein Y is $NR_3R_4$.

3. The process of claim 1, wherein $R_1$, $R_2$, $R_3$ and $R_4$ are independently selected from H, polyalkylamines, and polyamines.

4. The process of claim 1, wherein Y is $NR_3R_4$ and $R_1$, $R_2$, $R_3$ and $R_4$ are each H.

5. The process of claim 1, wherein X of formula (II) is fluorine.

6. The process of claim 2, wherein X of formula (II) is fluorine.

7. The process of claim 3, wherein X of formula (II) is fluorine.

8. The process of claim 4, wherein X of formula (II) is fluorine.

9. The process of claim 1, wherein said amine is an polyalkylamine, aminoalkylamino, hydrazine, polyamines or hydroxylamine.

10. The process of claim 9, wherein said polyalkylamine is $NR_1R_2H$, said hydrazine is $NH_2$—$NHR_1R_2$, and said hydroxylamine is $NH_2OR_1$.

11. The process of claim 9, wherein said amine is ammonium hydroxide.

12. The process of claim 1, wherein said 2-aminoadenine heterocycle is linked to ribose, deoxyribose, or a 2'-O-substituted ribose where said substituent is methoxyethyl, or dimethylaminooxyethyl.

13. The process of claim 1, wherein said oligonucleotide is bound to a solid support.

14. The process of claim 13, wherein said solid phase support is polystyrene or controlled pore glass.

15. The process of claim 12, wherein said 2-aminoadenine is incorporated into an oligonucleotide through the phosphoramidite method.

\* \* \* \* \*

UNITED STATES PATENT AND TRADEMARK OFFICE
CERTIFICATE OF CORRECTION

PATENT NO.   : 6,175,004 B1
DATED        : January 16, 2001
INVENTOR(S)  : Bruce S. Ross and Muthiah Manoharan It is certified that error appears in the above-identified patent and that said Letters Patent is hereby corrected as shown below:

<u>Column 4,</u>
Line 30, please delete "2-aminoadenosine and like moieties" and insert therefor -- 2-aminoadenosine-like moieties --
Line 64, please delete "Substituients" and insert therefor -- Substituents --

<u>Column 21,</u>
Line 60, please delete "multiple" and insert therefor -- Multiple --

<u>Columns 23-24,</u>
Table I, SEQ ID 6, please delete the "b" that appears after GA.
Table II, SEQ.ID. 8, please delete the number "421" and insert therefor -- 41 --

Signed and Sealed this

Third Day of December, 2002

JAMES E. ROGAN
*Director of the United States Patent and Trademark Office*

SEQUENCE LISTING

```
<160> NUMBER OF SEQ ID NOS:  8

<210> SEQ ID NO 1
<211> LENGTH: 20
<212> TYPE: DNA
<213> ORGANISM: Artificial Sequence
<220> FEATURE:
<221> NAME/KEY: modified_base
<222> LOCATION: (1)
<223> OTHER INFORMATION: 2-aminoadenosine
<221> NAME/KEY: modified_base
<222> LOCATION: (5)
<223> OTHER INFORMATION: 2-aminoadenosine
<221> NAME/KEY: modified_base
<222> LOCATION: (16)..(17)
<223> OTHER INFORMATION: 2-aminoadenosine
<221> NAME/KEY: misc_feature
<222> LOCATION: (1)..(6)
<223> OTHER INFORMATION: 2'-methoxyethyl
<221> NAME/KEY: misc_feature
<222> LOCATION: (15)..(20)
<223> OTHER INFORMATION: 2'-methoxyethyl
<223> OTHER INFORMATION: Description of Artificial Sequence: Novel
      Sequence
```

<400> SEQUENCE: 1
atgcattctg cccccaagga                                           20

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: (2)..(3)
<223> OTHER INFORMATION: 5-methyl
<221> NAME/KEY: modified_base
<222> LOCATION: (7)
<223> OTHER INFORMATION: 2-aminoadenosine
<221> NAME/KEY: misc_feature
<222> LOCATION: (9)
<223> OTHER INFORMATION: 5-methyl
<221> NAME/KEY: misc_feature
<222> LOCATION: (11)
<223> OTHER INFORMATION: 5-methyl
<221> NAME/KEY: misc_feature
<222> LOCATION: (13)..(14)
<223> OTHER INFORMATION: 5-methyl
<221> NAME/KEY: misc_feature
<222> LOCATION: (16)
<223> OTHER INFORMATION: 5-methyl
<221> NAME/KEY: modified_base
<222> LOCATION: (17)
<223> OTHER INFORMATION: 2-aminoadenosine
<223> OTHER INFORMATION: Description of Artificial Sequence: Novel
      Sequence

<400> SEQUENCE: 2
tccgtcatcg ctcctcaggg                                           20

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (2)..(4)
<223> OTHER INFORMATION: 5-methyl
<221> NAME/KEY: modified_base
<222> LOCATION: (5)..(6)
<223> OTHER INFORMATION: 2-aminoadenosine
<221> NAME/KEY: misc_feature
<222> LOCATION: (8)
<223> OTHER INFORMATION: 5-methyl
<221> NAME/KEY: misc_feature
<222> LOCATION: (12)
<223> OTHER INFORMATION: 5-methyl
<221> NAME/KEY: modified_base
<222> LOCATION: (13)
<223> OTHER INFORMATION: 2-aminoadenosine
<221> NAME/KEY: misc_feature
<222> LOCATION: (15)..(16)
<223> OTHER INFORMATION: 5-methyl
<221> NAME/KEY: misc_feature
<222> LOCATION: (19)
<223> OTHER INFORMATION: 5-methyl
<221> NAME/KEY: modified_base
<222> LOCATION: (20)
<223> OTHER INFORMATION: 2-aminoadenosine
<223> OTHER INFORMATION: Description of Artificial Sequence: Novel
      Sequence

<400> SEQUENCE: 3
gcccaagctg gcatccgtca                                           20

<210> SEQ ID NO 4
<211> LENGTH: 20

```
<212> TYPE: DNA
<213> ORGANISM: Artificial Sequence
<220> FEATURE:
<221> NAME/KEY: misc_feature
<222> LOCATION: (4)
<223> OTHER INFORMATION: 5-methyl
<221> NAME/KEY: misc_feature
<222> LOCATION: (6)
<223> OTHER INFORMATION: 5-methyl
<221> NAME/KEY: misc_feature
<222> LOCATION: (8)
<223> OTHER INFORMATION: 5-methyl
<221> NAME/KEY: modified_base
<222> LOCATION: (14)
<223> OTHER INFORMATION: 2-aminoadenosine
<221> NAME/KEY: misc_feature
<222> LOCATION: (19)
<223> OTHER INFORMATION: 5-methyl
<221> NAME/KEY: modified_base
<222> LOCATION: (20)
<223> OTHER INFORMATION: 2-aminoadenosine
<223> OTHER INFORMATION: Description of Artificial Sequence: Novel
      Sequence

<400> SEQUENCE: 4
gttctcgctg gtgagtttca                                              20

<210> SEQ ID NO 5
<211> LENGTH: 20
<212> TYPE: DNA
<213> ORGANISM: Artificial Sequence
<220> FEATURE:
<221> NAME/KEY: misc_feature
<222> LOCATION: (2)..(4)
<223> OTHER INFORMATION: 5-methyl
<221> NAME/KEY: misc_feature
<222> LOCATION: (6)..(7)
<223> OTHER INFORMATION: 5-methyl
<221> NAME/KEY: modified_base
<222> LOCATION: (12)
<223> OTHER INFORMATION: 2-aminoadenosine
<221> NAME/KEY: modified_base
<222> LOCATION: (14)
<223> OTHER INFORMATION: 2-aminoadenosine
<221> NAME/KEY: misc_feature
<222> LOCATION: (17)
<223> OTHER INFORMATION: 5-methyl
<221> NAME/KEY: modified_base
<222> LOCATION: (18)
<223> OTHER INFORMATION: 2-aminoadenosine
<223> OTHER INFORMATION: Description of Artificial Sequence: Novel
      Sequence
<221> NAME/KEY: misc_feature
<222> LOCATION: (13)
<223> OTHER INFORMATION: 5-methyl

<400> SEQUENCE: 5
tcccgcctgt gacatgcatt                                              20

<210> SEQ ID NO 6
<211> LENGTH: 17
<212> TYPE: DNA
<213> ORGANISM: Artificial Sequence
<220> FEATURE:
<221> NAME/KEY: modified_base
<222> LOCATION: (3)
<223> OTHER INFORMATION: 2-aminoadenosine
<221> NAME/KEY: modified_base
<222> LOCATION: (8)..(9)
<223> OTHER INFORMATION: 2-aminoadenosine
<221> NAME/KEY: modified_base
<222> LOCATION: (13)
<223> OTHER INFORMATION: 2-aminoadenosine
<221> NAME/KEY: modified_base
<222> LOCATION: (16)
```

```
<223> OTHER INFORMATION: 2-aminoadenosine
<223> OTHER INFORMATION: Description of Artificial Sequence: Novel
      Sequence

<400> SEQUENCE: 6
ggaccggaag gtacgag                                                      17

<210> SEQ ID NO 7
<211> LENGTH: 18
<212> TYPE: DNA
<213> ORGANISM: Artificial Sequence
<220> FEATURE:
<221> NAME/KEY: modified_base
<222> LOCATION: (9)
<223> OTHER INFORMATION: 2-aminoadenosine
<223> OTHER INFORMATION: Description of Artificial Sequence: Novel
      Sequence

<400> SEQUENCE: 7
ctcgtaccat tccggtcc                                                     18

<210> SEQ ID NO 8
<211> LENGTH: 21
<212> TYPE: DNA
<213> ORGANISM: Artificial Sequence
<220> FEATURE:
<221> NAME/KEY: modified_base
<222> LOCATION: (1)
<223> OTHER INFORMATION: 2-aminoadenosine
<221> NAME/KEY: modified_base
<222> LOCATION: (5)
<223> OTHER INFORMATION: 2-aminoadenosine
<221> NAME/KEY: modified_base
<222> LOCATION: (8)
<223> OTHER INFORMATION: 2-aminoadenosine
<221> NAME/KEY: modified_base
<222> LOCATION: (11)
<223> OTHER INFORMATION: 2-aminoadenosine
<221> NAME/KEY: modified_base
<222> LOCATION: (18)
<223> OTHER INFORMATION: 2-aminoadenosine
<223> OTHER INFORMATION: Description of Artificial Sequence: Novel
      Sequence

<400> SEQUENCE: 8
accgaggatc atgtcgtacg c                                                 21
```